Dec. 23, 1958 E. S. BOERNER Plant Pat. 1,783
ROSE PLANT
Filed April 28, 1958
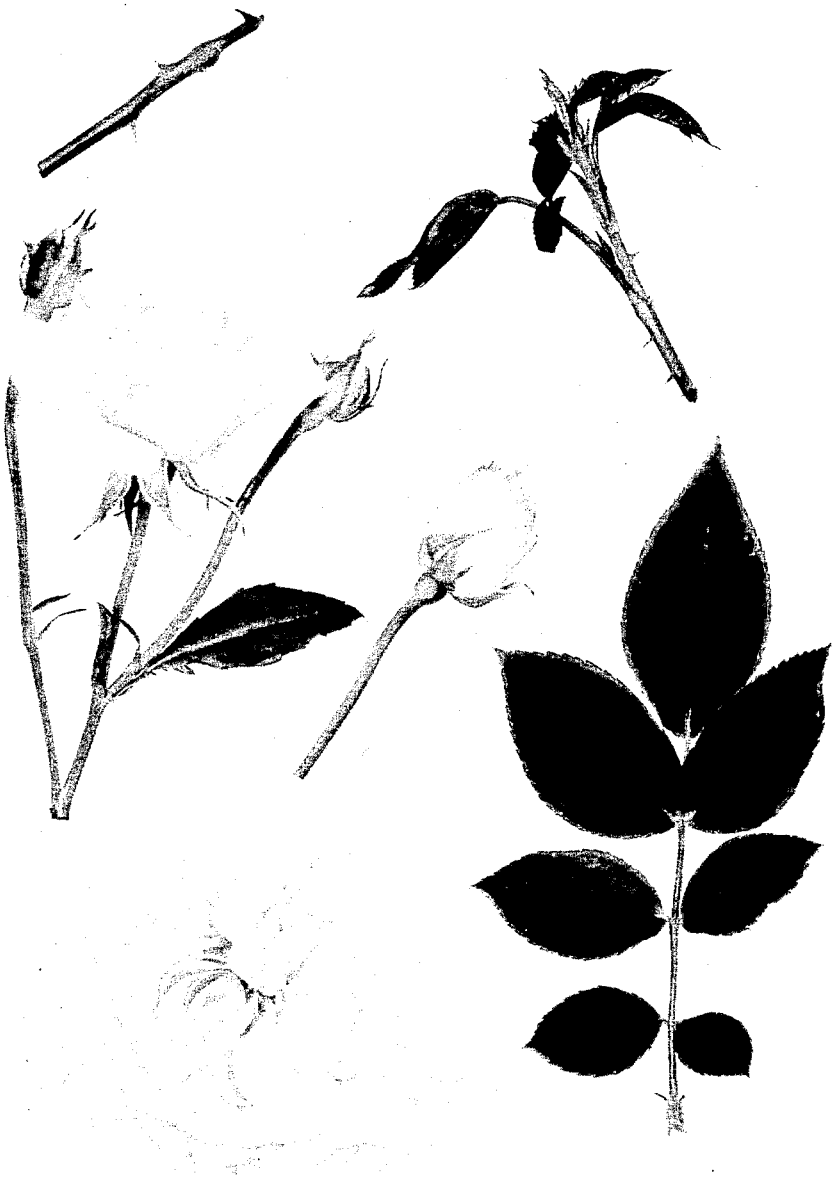
Inventor.
E. S. Boerner
By: Robb & Robb
Attorneys.

United States Patent Office

Plant Pat. 1,783
Patented Dec. 23, 1958

1,783

ROSE PLANT

Eugene S. Boerner, Newark, N. Y., assignor to Jackson & Perkins Company, Newark, N. Y., a corporation of New York Application April 28, 1958, Serial No. 731,557

1 Claim. (Cl. 47—61)

The present invention relates to a new and distinct variety of rose plant of the large-flowered polyantha class, which was originated by me by re-crossing the variety "Demure" (Plant Patent No. 1,065) with "Demure."

The primary objective of this breeding was to obtain a larger-flowered and stronger-stemmed form of the parent variety "Demure." This objective was fully achieved, along with other improvements, as evidenced by the following unique combination of characteristics which are outstanding in the new variety and distinguish it from its parent, as well as from all other varieties of which I am aware:

(1) A vigorous habit of plant growth;

(2) Vigorous and prolific production of flowers under ordinary greenhouse conditions, with the flowers borne on stems of unusually good strength;

(3) Large, high-centered and full-petalage form of the flowers; and (4) A distinctive La France Pink, lightly overcast with Shrimp Pink, general color tonality of the flowers.

Asexual reproduction of my new variety, by budding, as performed at Newark, New York and also at Pleasanton, California, shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Demure."
*Pollen parent.*—"Demure."
Classification:
*Botanic.*—Large-flowered polyantha.
*Commercial.*—Floribunda.

*Flower*

(Observations made from specimens grown in a greenhouse at Newark, New York in the late morning near mid-February.)

Blooming habit: Recurrent—continuous.
Bud:
*Size.*—Medium.
*Form.*—Ovoid; is not affected by wet or hot weather.
*Color.*—When sepals first divide—Eugenia Red, Plate 13. When petals begin to unfurl—Thulite Pink, Plate 26, lightly overcast with La France Pink, Plate 1. When half-blown: inside of petals—Shrimp Pink, Plate 1, with edges of petal lightly overcast with La France Pink, Plate 1; reverse of petals—La France Pink, Plate 1.
*Sepals.*—Slightly branched; curl back when petals begin to unfurl. Color: inside—Kildare Green, Plate 31; outside—Light Cress Green, Plate 31.
*Calyx.*—Color—Absinthe Green, Plate 31. Shape—pear. Size—small. Aspect—smooth. Odor when rubbed—none.
*Peduncle.* — Length — medium. Aspect — smooth. Strength—erect; slender. Color—Yellowish Oil Green, Plate 5.
*Opening.*—Opens up well; is not affected by adverse weather conditions.

Bloom:
*Size.*—Medium. Average size when fully expanded—3½ inches.
*Borne.*—Both singly and in rounded clusters.
*Stems.*—Medium length; strong.
*Form (when first open).*—From cupped to high-centered. Permanence—retains its form to the end.
*Petalage.*—Double (full but open center). Number of petals under normal conditions—from 55 to 60.
*Color.*—Center of flower—Eosine Pink, Plate 1, lightly overcast with Shrimp Pink, Plate 1. Outer petals—Hermosa Pink, Plate 1. Base of petals (aiglet)—Sea-Foam Yellow, Plate 31. Inside of petals—La France Pink, Plate 1, lightly overcast with Shrimp Pink, Plate 1. Reverse of petals—Shrimp Pink, Plate 1. General tonality from a distance—La France Pink, Plate 1, lightly overcast with Shrimp Pink, Plate 1.
*Discoloration.*—General tonality at end of first day—Eosine Pink, Plate 1, lightly overcast with Shrimp Pink, Plate 1. Second day—Eosine Pink, Plate 1, overcast with Shrimp Pink, Plate 1. Third day—La France Pink, Plate 1.
Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; small.
*Persistence.*—Drop off cleanly.
*Fragrance.*—Strong. Nature—"Old Rose perfume" (centifolia).
*Lasting quality.*—On the plant—very long. As cut flower—very long.

*Genital organs*

Stamens, anthers: Small; few; mixed with petaloids. Color—Light Orange Yellow, Plate 3.
Stamens, filaments (threads): Medium length. Color—Sea-Foam Yellow, Plate 31.
Pollen: Color—Pale Yellow-Orange, Plate 3.
Styles: Loosely separated; uneven length; medium length; thin.
Stigmas: Color—Chartreuse Yellow, Plate 31.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Medium.
*Quantity.*—Normal.
*Color.*—New foliage: upper side—Oxblood Red, Plate 1; under side—Bordeaux, Plate 12. Old foliage: upper side—Cress Green, Plate 31; under side—Light Elm Green, Plate 17.
*Shape.*—Oval pointed.

*Texture.* — Upper side — leathery. Under side—smooth.

*Ribs and veins.*—Ordinary.

*Edge.*—Serrated (saw-toothed).

*Serration.*—Both double and single; small.

*Leaf stem.*—Color—Light Cress Green, Plate 31. Under side—prickly.

*Stipules.*—Medium length; smooth.

Wood:

*New wood.* — Color — Absinthe Green, Plate 31. Bark—smooth.

*Old wood.*—Color—Cress Green, Plate 31. Bark—smooth.

Thorns:

*Thorns.*—Quantity: on main stalks from base—few; on laterals from stalk—few. Form—narrow base; medium length; hooked downward. Color (when young)—Chartreuse Yellow, Plate 31. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of vigorous plant growth, vigorous and prolific production of flowers under ordinary greenhouse conditions, with the flowers borne on stems of unusually good strength, large, high-centered and full-petalage form of the flowers, and a distinctive La France Pink, lightly overcast with Shrimp Pink, general color tonality of the flowers.

No references cited.